United States Patent [19]

Delay

[11] 4,252,728
[45] Feb. 24, 1981

[54] NORBORNANE AND NORBORNENE DERIVATIVES

[75] Inventor: Francois Delay, Geneva, Switzerland

[73] Assignee: Firmenich SA, Geneva, Switzerland

[21] Appl. No.: 28,843

[22] Filed: Apr. 10, 1979

[30] Foreign Application Priority Data

Apr. 17, 1978 [CH] Switzerland .......................... 4073/78

[51] Int. Cl.³ .......................................... C07D 303/48
[52] U.S. Cl. ............................. 260/348.58; 252/522 R
[58] Field of Search ........................ 260/348.17, 348.58

[56] References Cited

U.S. PATENT DOCUMENTS

| 2,889,339 | 6/1959 | Levy | 260/348.58 |
|---|---|---|---|
| 4,007,217 | 2/1977 | Kogure et al. | 260/348.17 |

FOREIGN PATENT DOCUMENTS 2163770  7/1973  Fed. Rep. of Germany .

*Primary Examiner*—Norma S. Milestone

[57] ABSTRACT

New norbornane (-ene) derivatives of formula

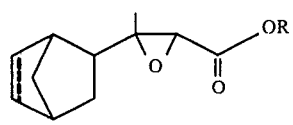

(Ia,b)

containing a single or a double bond in the position indicated by the dotted line and wherein symbol R represents a lower alkyl radical having 1 to 4 carbon atoms, find a useful application as perfuming ingredients for the manufacture of perfumes and perfumed products.

3 Claims, No Drawings

NORBORNANE AND NORBORNENE DERIVATIVES

THE INVENTION

The present invention relates to a process for imparting, modifying or enhancing the odoriferous properties of perfumes and perfumed products, which process comprises the step of adding thereto a perfuming effective amount of a compound of formula

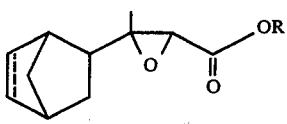
(Ia,b)

containing a single or a double bond in the position indicated by the dotted line and wherein symbol R represents a lower alkyl radical having 1 to 4 carbon atoms.

The invention provides also a perfume composition which is characterized by having incorporated an odour effective amount of a compound of formula (Ia, b).

The invention relates also to a perfume or a perfumed product containing an odour effective amount of a compound of formula (Ia, b).

Finally, the invention provides a process for the preparation of a compound of formula

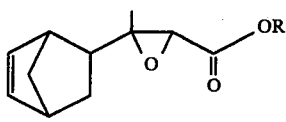
(Ia)

wherein symbol R represents a lower alkyl radical having 1 to 4 carbon atoms, which comprises reacting, in the presence of a strong base, acetyl-norbornene with an alkyl chloroacetate of formula

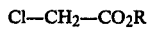     (II)

wherein R has the above given meaning.

BACKGROUND OF THE INVENTION

The compounds of formula (Ia, b) belong to the class of esters of glycidic acid. Preferred examples of these compounds when used in accordance with the invention are the methyl and the ethyl esters, viz. methyl 3-methyl-3-(norbornen-5-yl)-glycidate and ethyl 3-methyl-3-(norbornen-5-yl)-glycidate which compounds develop the most pronounced fragrance.

Compounds possessing a chemical structure analogous to that of compounds (Ia, b) and having been described in the art as possessing odoriferous properties include acetyl-norbornene of formula

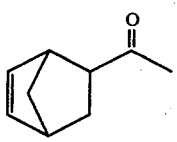

(see Japanese Pat. No. 71 30 184), and 5-(2-alkoxycarbonylvinyl)-bicyclo[2.2.1]hept-2-ene of formula

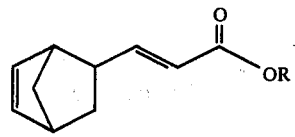

(see DE-OS No. 21 63 770 published on July 5, 1973). No well defined indication has been given with respect to the olfactive properties of the first one of the above defined compound; whereas the cited bicyclo-heptene compound is described as possessing a fruity odour reminiscent of that developed by melon.

When I tried to synthesize 5-(2-ethoxycarbonyl-vinyl)-bicyclo[2.2.1]hept-2-ene in accordance with the described method, instead of the expected product I obtained a complex mixture containing about 60% of the pure compound, which upon isolation and purification did not possessed, contrary to the prior art teaching, any melon-like smell.

I have now discovered that compounds (Ia, b) present in contradistinction a fruity fragrance whose melon-like character is well distinct and perfectly reproducible. Consequently, the compounds of formula (Ia, b) present a major interest for perfumery, not only for the manufacture of perfume compositions destined to the preparation of perfumes, but also as active ingredients for perfuming various articles, such as soaps, cosmetics, shampoos, body deodorizers, air fresheners, waxes, detergents or household materials in general.

PREFERRED EMBODIMENTS OF THE INVENTION

The odour of the compounds of the invention is particularly tenacious. Its character is eminently fruity, more specifically of melon-like type, with nuances reminiscent of strawberries or even peaches. The overall odour character is very pleasant, fresh and elegant and, consequently, the use of the compounds of formula (Ia, b) is rather broad.

The glycidates of the invention can be used on their own as perfuming agents, or in compositions comprising one or more other perfuming coingredients, in the form of diluted or concentrated solutions in the solvents commonly employed for this purpose, e.g. diethyl phthalate or ethanol.

The concentrations at which the perfuming agents of formula (Ia, b) are used can vary widely, depending on the specific odourous effect it is desired to achieve and the type of material to which they are added.

Useful perfuming effects can generally be achieved with concentrations of from about 1 to 20, or even 30% by weight based on the total weight of the perfumed article or perfume composition to which they are added. It is to be understood however that the said concentration values have not to be interpreted in a restrictive way and higher or lower concentrations can be used for special purposes.

The glycidates of formula (Ia, b) are easily obtained starting from a commercially available product, acetyl-norbornene, according to a process which comprises reacting it with an alkyl chloroacetate in the presence of a strong base, e.g. an alkali metal alkoxide such as sodium or potassium methoxide or ter-butoxide. The said process is summarized in the hereinbelow reaction scheme:

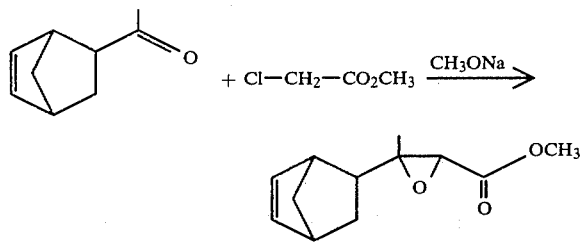

Of course, the reaction proceeds in an analogous manner by replacing methyl chloroacetate, such as indicated in the above scheme, by its higher homologs, ethyl or butyl chloroacetate, to give in such cases the corresponding ethyl and butyl glycidates.

Formula (Ia, b) is deemed to define the various possible conformational isomers; eight different stereoisomers can in fact be formulated. The product such as obtained by the above described process consists in a mixture of isomers whose composition however is well defined and reproducible.

These mixtures are perfectly suitable for all practical purposes envisaged in perfumery. Nonetheless, whenever required, the different isomers can be separated by making use of conventional techniques, such as e.g. preparative vapour phase chromatography.

The compounds of formula (Ib) having a single bond in the ring, i.e. the alkyl esters of norbornane, can be prepared by simple reduction of the corresponding unsaturated derivatives, e.g. by catalytic hydrogenation in the presence of current catalysts such as palladium on charcoal.

The invention is better illustrated by but not limited to the following examples wherein the temperatures are given in degrees centigrade.

EXAMPLE 1

59.9 g (0.55 mole) of methyl chloroacetate were added dropwise to a suspension of 50 g (0.367 mole) of acetyl norbornene and 29.7 g (0.55 mole) of sodium methoxide. The addition lasted 3 hours and was kept at such a rate as to maintain the temperature at a value below +5°, whereupon the temperature was increased to +10° and kept at this value for 2 hours while stirring. The reaction mixture was then left under further stirring overnight at room temperature and, poured then onto a mixture of icy water (500 ml) and ether (220 ml). The organic phase was separated and combined with the organic ether extracts resulting from the extraction of the aqueous part (3 fractions of 50 ml each of ether), washed with 1% aqueous HCl (200 ml) with water (3×50 ml) and finally with a saturated aqueous solution of NaCl. After drying over anhydrous sodium sulfate and evaporation under reduced pressure, there was obtained a residue which upon distillation gave 53.7 g (0.258 mole) of the desired product (yield=70.3%).

IR(film, liquid): 3060, 1752, 1730, 1600, 1200, 1080 and 1035 cm$^{-1}$;

NMR(CDCl$_3$): 1.1-2.0 (8H); 2.6-3.1 (2H, m); 3.12/3.31/3.39 and 3.57 (1H, 4s); 3.79 (3H, several s); 5.9-6.3 (2H, m) δ ppm;

MS: M$^+$=208 (1); m/e: 190 (1), 149 (8), 131 (8), 119 (5), 105 (5), 91 (10), 83 (15), 66 (100), 55 (15), 43 (12), 41 (8), 39 (12).

By carrying out the reaction according to the above described process and replacing methyl chloroacetate by ethyl chloroacetate, the corresponding ethyl ester, i.e. ethyl 3-methyl-3-(norbornen-5-yl)-glycidate, was obtained with analogous yield. The obtained product possessed the following analytical characters:

IR(film, liquid): 3060, 1750, 1730, 1605, 1200, 1080 and 1035 cm$^{-1}$;

NMR(CDCl$_3$): 1.1-1.6 (11H, m); 2.6-3.1 (2H, m); 3.1 (2H, m); 3.20/3.31/3.38 and 3.56 (1H, 4s); 4.28 (2H); 5.9-6.3 (2H, m) δ ppm;

MS: M$^+$=222 (2); m/e: 204 (2), 189 (1), 162 (5), 149 (7), 131 (6), 119 (5), 111 (6), 91 (15), 83 (17), 66 (100), 55 (15), 43 (22).

The reduction effected by catalytic hydrogenation of the esters derivatives of norbornene gave the corresponding saturated derivatives:

methyl 3-methyl-3-norbornyl-glycidate

IR(film, liquid): 1745, 1730, 1305, 1200, 1080 and 1025 cm$^{-1}$;

NMR(CDCl$_3$): 0.95-2.0 (12H); 2.05-2.6 (2H, 2m); 3.15/3.36/3.5 (1H, 3s); 3.79 (3H, several s) δ ppm;

MS: M$^+$=210 (2); m/e: 192 (2), 181 (30), 151 (60), 133 (15), 122 (40), 107 (23), 93 (100), 79 (68), 67 (65), 55 (30), 43 (45) and 41 (46).

ethyl 3-methyl-3-norbornyl-glycidate

IR(film, liquid): 1750, 1730, 1305, 1195, 1083 and 1035 cm$^{-1}$;

NMR(CDCl$_3$): 0.9-2.0 (15H); 2.1-2.55 (2H, 2m); 3.12/3.31/3.48 (1H, 3s) and 4.25 (2H, q, J=7.5 cps) δ ppm;

MS: M$^+$=224 (4); m/e: 206 (3), 195 (32), 167 (22), 151 (78), 133 (20), 122 (50), 107 (25), 93 (100), 79 (60), 67 (65), 55 (30), 43 (55), 41 (46).

EXAMPLE 2

Perfuming of detergent powder

A commercial sample of detergent powder was perfumed by making use of 0.2% by weight of methyl 3-methyl-3-(norbornen-5-yl)-glycidate, as prepared by the process of Example 1. The perfumed product thus obtained possessed a fresh and pleasant fruity melon-like odour.

EXAMPLE 3

Air freshener 15 ml of a 4% alcoholic solution of methyl 3-methyl-3-(norbornen-5-yl)-glycidate were introduced in an aerosol container together with 85 ml of propellant (FRIGEN® 11/12). The thus obtained deodorizing article enabled the rapid perfuming of a room by imparting a fruity, melon-like fragrance.

EXAMPLE 4

A base perfume composition of "bouquet de fleurs" type was prepared by mixing the following ingredients (parts by weight)

| | |
|---|---|
| α-Amyl cinnamic alcohol | 150 |
| Hydratropic alcohol | 100 |
| α-Amyl cinnamic aldehyde | 80 |
| 3,3,5-Trimethylhexyl acetate | 80 |
| Nerol | 60 |
| Citronellyl isobutyrate | 40 |
| p-ter-Butylcyclohexyl acetate | 40 |
| Nonenol 1%* | 40 |
| Benzyl acetate | 30 |
| Phenoxyethyl isobutyrate | 20 |
| Dimethyl phenyl ethylcarbinol | 20 |

| -continued | |
|---|---|
| Geranyl ethyl ether | 20 |
| Nonadienol 1%* | 20 |
| | 700 |

*in diethyl phthalate

The above base composition possesses a fresh and flowery odour note and is particularly adapted to perfume toilet soaps or shampoos. By adding to 70 g of this base composition, 30 g of methyl 3-methyl-3-(norbornen-5-yl)-glycidate, or an equivalent amount of its ethyl ester, the characteristic neat flowery note is converted into a distinct and pleasant flowery, melon-like one.

EXAMPLE 5

Methyl 3-methyl-3-(norbornen-5-yl)-glycidate was used to perfume current cosmetic articles such as shampoos and hydrating creams at a concentration of 0.2% by weight based on the total weight of the perfumed articles. The thus obtained materials presented a fresh, fruity and particularly pleasant fragrance of good stability.

The same methyl ester at a concentration of 5% in 95% ethanol was used for the manufacture of an eau-de-toilette.

Analogous effects were obtained by substituting the ethyl and the butyl ester for methyl 3-methyl-3-(norbornen-5-yl)-glycidate, however, in this case the effects achieved were less pronounced.

What I claim is:

1. A compound of formula

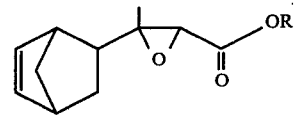

wherein symbol R represents a lower alkyl radical having 1 to 4 carbon atoms.

2. Methyl 3-methyl-3-(norbornen-5-yl)-glycidate.
3. Ethyl 3-methyl-3-(norbornen-5-yl)-glycidate.

* * * * *